United States Patent [19]

Oeste

[11] Patent Number: 5,627,353

[45] Date of Patent: May 6, 1997

[54] SPHERES CONTAINING ACTIVE COMPOUNDS, THEIR SYNTHESIS AND THE METHOD OF OPENING THE SPHERES

[75] Inventor: Franz D. Oeste, Kirchhain-Schönbach, Germany

[73] Assignee: Udo Schlagwein, Bad Nauheim, Germany

[21] Appl. No.: 165,927

[22] Filed: Dec. 14, 1993

[30] Foreign Application Priority Data

Dec. 15, 1992 [DE] Germany .......................... 42 42 216.7

[51] Int. Cl.⁶ .................................................. C07C 61/00
[52] U.S. Cl. ................. 204/157.15; 604/20; 423/445.13; 423/447.2; 540/467; 540/470
[58] Field of Search ...................... 204/157.15; 604/20; 423/445 B, 447.2; 540/467, 470

[56] References Cited

U.S. PATENT DOCUMENTS 5,350,569   9/1994   Coppa ........................................ 423/251
5,453,413   9/1995   Eklund ....................................... 502/416

FOREIGN PATENT DOCUMENTS 9315768   8/1993   WIPO.

OTHER PUBLICATIONS

Abstract to WO 93/15768.

*Primary Examiner*—Cecilia J. Tsang
*Assistant Examiner*—C. Delacroix-Muirheid
*Attorney, Agent, or Firm*—Evenson, McKeown, Edwards & Lenahan P.L.L.C.

[57] ABSTRACT

Spheres with a tetrahedral, octahedral and icosohedral geometry containing active compounds, wherein the spheres embrace the same volume as the fullerenes of the same symmetry, and are described by the formulas $C_{360}N_{240}O_{24}U_{12}$, $C_{1080}H_{300}N_{120}O_{24}U_{12}$, $C_{144}N_{96}Cu_{14}$ and $C_{432}H_{132}N_{48}$, their synthesis, the method of liberating the active compounds by irradiating the spheres to destroy the spheres such to release the active compounds, as well as possible uses for spheres filled with active compounds.

5 Claims, No Drawings

5,627,353

SPHERES CONTAINING ACTIVE COMPOUNDS, THEIR SYNTHESIS AND THE METHOD OF OPENING THE SPHERES

SUMMARY

Spheres with a tetrahedral, octahedral and icosohedral geometry containing active compounds, that embrace the same volumes as the fullerenes of the same symmetry, and that are described in formulas 1), 2) and 3), their synthesis, the method of liberating the active compounds, as well as possible uses for the spheres filled with active compounds. Spheres containing active compounds, their synthesis and the method of opening the spheres.

The spheres are hollow molecules of tetrahedral, octahedral or icosohedral geometry belonging to the group of heterofullerenes, fullerenes, fragments of hetero-fullerenes or fragments of fullerenes. The topography of empty spheres, as well as their synthesis and their use, are described in the German patent applications 41 14 536.4 and 41 28 357.0. The diameter of the spheres may vary between 1 nm and 10 nm. The hollow molecules may, according to the German patent application 41 14 536.4, be filled with monomers which pass through aggregate apertures in the spheres; the apertures may thereafter be closed through metal complexes. The monomers should be freed from the spheres through the chemically induced opening process of the hollow molecules, through the thermal decomposition of the spheres or through decomplexing of the metals or metalloids closing the apertures.

The method of enclosing the monomers, as well as the method of freeing them through chemical manipulations of the spheres prepared to this effect, show a number of drawbacks:

1. Only monomers that can pass through the apertures consisting of molecules capable of forming complexes, may be enclosed in the spheres according to this method.

2. At least two steps are necessary in order to enclose the monomers in the spheres according to the chemical method, i.e. the filling of the sphere and the closing of the aperture.

3. The opening of the spheres through a decomplexing step requires the use of aggressive chemicals, e.g. sulphuric acid. The use of high external temperature is necessary in order to induce a thermal decomposition of the spheres. Both methods, but to a larger extent the thermal method, require sacrifice of time, i.e. the reaction is not instantaneous.

The task to find a method that does not have these drawbacks thus remains. Using the invented method, we surprisingly succeeded in opening up the spheres instantaneously and in a targetted manner, without the use of external heat, nor the use of decomplexing agents. In addition, it is possible to produce filled spheres in one step, using the invented method, whereby the introduced molecule may have a diameter corresponding to the maximum of the internal diameter of the spheres.

According to the invented method, the filled spheres are opened within the fraction of a second through the use of electromagnetic radiations of adequate energy, and thereby release the stored compounds. Appropriate photons are those that can be absorbed by the filled spheres. These are generally photons of a wavelength between 200 nm and 1000 nm, which encompasses the visible range. It is as a rule sufficient to use radiation of the intensity necessary to bring water to the boil in order to open the spheres. Small spheres need a higher intensity of radiation in order to open up than larger spheres. Spheres with tightly meshed cage structures need higher radiation intensities to open up as those with large meshed structures. Spheres containing materials that already are under pressure may be opened using less radiation intensity than those filled with materials that are not under pressure.

In contrast to the known method of filling the spheres through the complexing apertures, the spheres may be filled, according to the invented process, by non spherical adducts during the synthesis of the spheres. According to this method, materials which do not impede the synthesis of the spheres and which fit into the spheres in terms of size and shape, may be enclosed in the spheres. This also applies to molecules dispersed in the fluid in which the spheres are synthesised.

Corresponding to a development of the invented method, spheres filled in such a way may be subjected to further chemical manipulations, e.g. the jointing of a tightly meshed surface, the modification of the surface of the sphere or the anchoring of substances to the surface of the sphere.

Corresponding to a further development of the invented method, decomposable substances may on their own, or together with non decomposable substances, be enclosed in the spheres, e.g. explosives. Through this method it is possible to minimise the radiation energy necessary to open up the spheres.

Corresponding to a further development of the invented method, the spheres may be filled with substances that contain radioactive elements.

In order not to restrict the spectrum of the photons to the ones that are absorbed by the molecular structure of the spheres and that are transformed into perceptible heat, it may be advantageous to fill the spheres with compounds that absorb photons in those regions of the spectrum to which the molecular structure of the spheres is transparent. It is usually sufficient that these photon absorbing materials are present as an adjunct to the materials filling the spheres.

Examples of possible uses are enumerated below in order to show the wide possible uses of the invented method.

Explosive materials:

When thermally labile materials like nitromethane, nitrobenzol, dinitrobenzol, tetrazol are used as constituent parts of the filling of the spheres, then these may be used as for example detonators that can be ignited from a distance through the use of a laser beam.

Oxygen loaded spheres mixed with substances capable of being oxidised, or spheres loaded with substances capable of being reduced mixed with oxidising substances, or in the presence of a redox catalyst, e.g. Palladium, may equally be used as detonators to be ignited through a laser beam.

Lithography, information storage, copiers, microelectronics:

Spheres filled with reactive materials induce the liberation of reactive compounds like Gallium, Indium, Antimony or Arsenic through the opening of a chemically modified environment, e.g. precipitation of metals, into an environment coated with reactive materials. Microscopically precise structures may then be produced through the use of short wave radiation (e.g. U.V., X-rays, electrons).

The images and structures may be represented in three dimensions through the use of appropriate focussing techniques using lenses or holographic methods. Spheres that are filled with hardening agents, and uniformly distributed throughout a block of synthetic resin, may in this way be opened following a planned pattern, whereby they induce the hardening process in their immediate surroundings. The three-dimensional structure is revealed through the subsequent dissolution of the non-hardened resin.

Novel materials:

Through their near spherical geometry and through the use of a particular type of sphere, it is possible to build two or three dimensional lattice structures. The free volumes between the spheres may then be filled with polymerising or polycondensing materials, e.g. silicofluoric acid, titanic acid, acrylic acid or ester, which then polymerises or polycondensates. The spheres may thereafter be destroyed and extracted from the lattice through oxidation or, for example, through supercritical gas extraction. It is possible to produce molecular sieves, catalysator supports, optical lattices, information storage, selective membranes etc. using this method. Carriers of medically active materials:

Spheres containing medically active materials, and where the surfaces of the spheres have been subjected to a specific chemical modification in order to obtain an optimal biochemical affinity with the target tissue, are suitable for use in the treatment of targetted organs or tissues. Owing to the fact that the medicament is exclusively released within the target tissue, the dose can remain extremely small, although optimally calculated in terms of the target tissue, thus reducing the danger of side effects on non treated tissues. This is possible because the medicament is hermetically enclosed within the spheres and thereby remains inactive as the physiological breaking-down mechanism is not able to open up the closed spheres, even over a long period of time. This distinguishes the spheres from the up to now tested microcapsules made of synthetic materials, which are more or less rapidly broken down by the body. The spheres display the added advantage of having a small size; approximately three times less than micro capsules. The advantage of using spheres is shown through the example below concerning the treatment of cancer.

Spheres are synthesised in the presence of cellular poisons, e.g. ammonia, phosgene or carbon disulphide. A radioactive marker is also added to the reaction mixture, e.g. methyl iodide containing the active isotope $I^{131}$, which is then enclosed within the spheres. The filled spheres are thereafter rendered hydrophilic, if enough hydrophilic functions are not available through the construction of the spheres. The spheres have a great intrinsic affinity to cancerous cells due to the fact that they contain porphyric constituents. This is conform with the affinity of porphyrins and phthalcyanins with cancerous cells. It may be advantageous to coordinate, or to chemically couple the spheres with the carboxyl groups belonging to segments of cancer cell antibodies, thus tying each antibody to a sphere and increasing the affinity for cancer cells. It is thus possible to achieve a nearly quantitative absorbtion of the spheres filled with cellular poisons to the cancer cells. Spheres synthesised in this manner are injected in the circulatory system of the body. The location of the cancer cells loaded with spheres can be monitored through the radiation emitted by the iodide marker. When the activity of the cancer cells does not increase any more, the opening of the spheres containing the cellular poison may be undertaken. This can advantageously be done through the use of glass fibre optics, in order to reduce the amplitude of the intervention to a minimum. It is also advantageous to use a photon radiation in the visible part of the red spectrum in order to minimise disturbances through tissue absorbtion. It is possible to use the glass fibre optic installation mentioned above to send a "search beam" in order to ease the operator's visual search for the conglomerate of spheres. The strong coloration of the spheres renders their localisation easier. This method is appropriate to localise small tumors and metastases. It is possible to shorten the treatment of such cancers, or to carry out an ambulant treatment, using today's glass fibre optics and probes, and this without subjecting the patient a heavy classical chemical treatment. Due to the instantaneous destruction of the cancerous tissues, the destroyed cells, the remains of the spheres and the remains of the toxic chemicals can be aspirated through the probe and any damaged blood vessels may be cauterised through subsequent intensive radiations.

Spheres particularly suitable for these purposes are for example the spheres $C_{360}N_{240}O_{24}U_{12}$ (1) and $C_{1080}H_{300}N_{120}O_{24}U_{12}$ (2). The sphere (1) ecompasses the same volume as the symmetrically identical icosahedral fullerene $C_{960}$. The sphere (2), which also has a icosahedral symmetry, encompasses the same volume as the symmetrically identical sphere $C_{1620}$, which has a diameter of 4 nm. It is possible to produce smaller spheres at lesser costs, contrary to the sphere (2). The sphere $C_{144}N_{96}Cu_{14}$ (3) which displays an octahedral symmetry and has a volume corresponding to that of the symmetrically identical fullerene $C_{372}$, belong to these. So does the sphere $C_{432}H_{132}N_{48}$ (4) which encompasses a volume corresponding to the symmetrically identical fullerene $C_{636}$.

In contrast to the fullerenes which are built exclusively from hexagonal or pentagonal networks, these spheres consist of non flat aromatic surfaces displaying numerous possibilities of substitution or coordination of functional groups on the three times coordinated C—, N— or O— molecules, on which it is possible to attach any functions with particular affinity for a chosen tissue, in order that a sphere filled with medicaments may be used with a minimum of wastage. The function (5), which is contained between 4 and 30 times in the spheres, is of particular importance in this context.

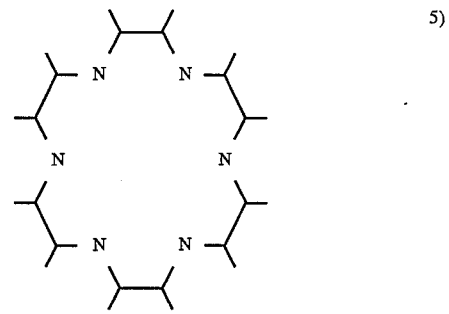

Further to the invented method of enclosing monomers within the spheres during their synthesis and further to the already known method of introducing the monomers through the porphyrin, subporphyrin or superporphyrin functions or through the crownether functional groups or through the crownether related functional groups, e.g. (5), it is possible, through a further variation of the invented method, to introduce the monomers into the spheres through the non polar apertures limited by CH— functions, and this shortly before or during the time the aperture is being closed by substrates. This method may be advantageous when the monomers are unstable in the conditions of synthesis of the spheres.

The examples below clarify the invented method, without however limiting the method to these examples.

EXAMPLE 1

The conversion of spheres containing functional groups according to formula (6), to which for example the spheres (2) and (4) referred to above belong, with bromocyanide instead of aluminium chloride at 70° C. to 90° C. according to the method published in Helv. Chem. Acta 2, 1919, pages 482 and following.

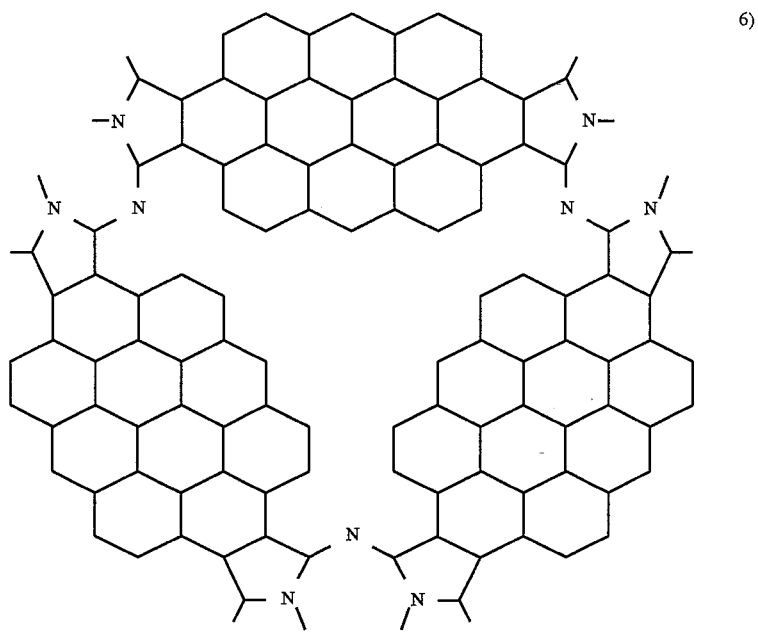

6)

The reaction is however carried out at a pressure of 300 bar, in contrast to the published method. Due to these conditions, the spheres are filled with bromocyanide, hydrogen bromide and small amounts of aluminium chloride and hydrochloric acid. The apertures are at the same time converted into function (7) through the release of hydrogen bromide.

functions according to formula (8). The mixture is decompressed and cooled to ambient temperature after 2 hours reaction time, thereafter filtered and the solids are washed several times with acetone and dried. The aluminium chloride function may be used for a further conversion of the spheres.

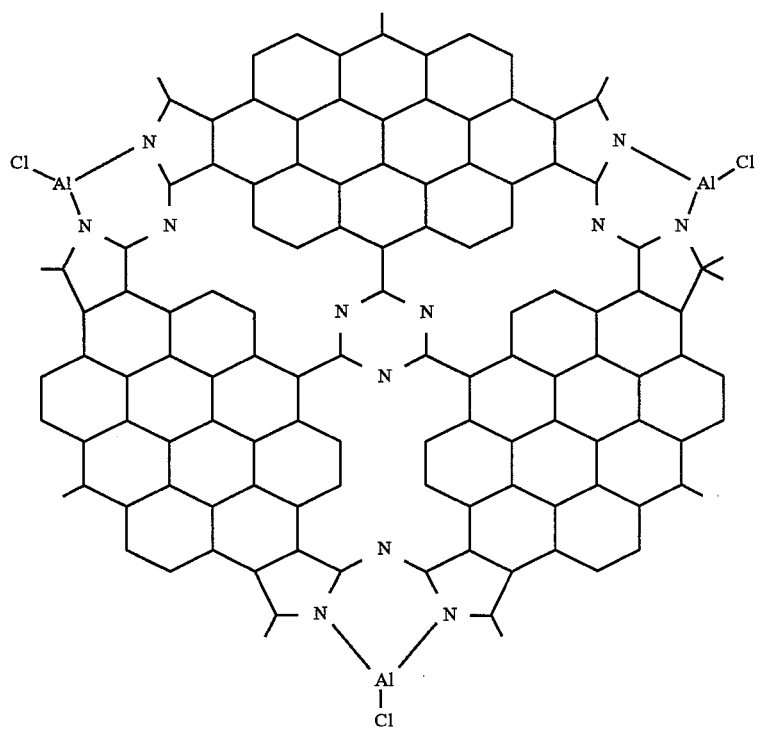

7)

In cases where the spheres contain porphyrin or superporphyrin metal complexes which are easily decomplexed, or in cases where they do not contain complexed metals, then the spheres are complexed with aluminium chloride 8)
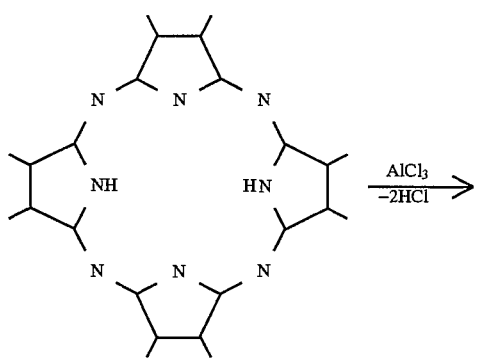

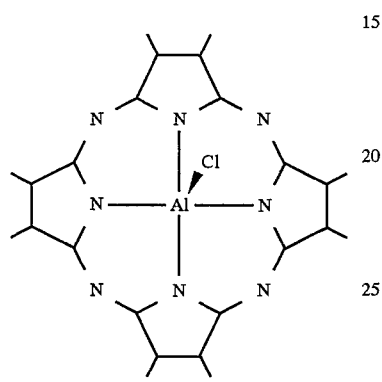

EXAMPLE 2

The function shown in the partial formula (7) can be built into an even larger lattice. This may for example be necessary when the opening of the spheres should take place at a higher radiation energy. The spheres, filled with mostly bromocyanide according to example 1, are slurried with ammonium dichloride and brought to react for 1 hour at 90° C. The mixture is subsequently filtered and the solids obtained washed several times with acetone and dried. The partial formula (9) defines the product of the reaction, containing a preponderance of products filled with bromocyanide.

9)
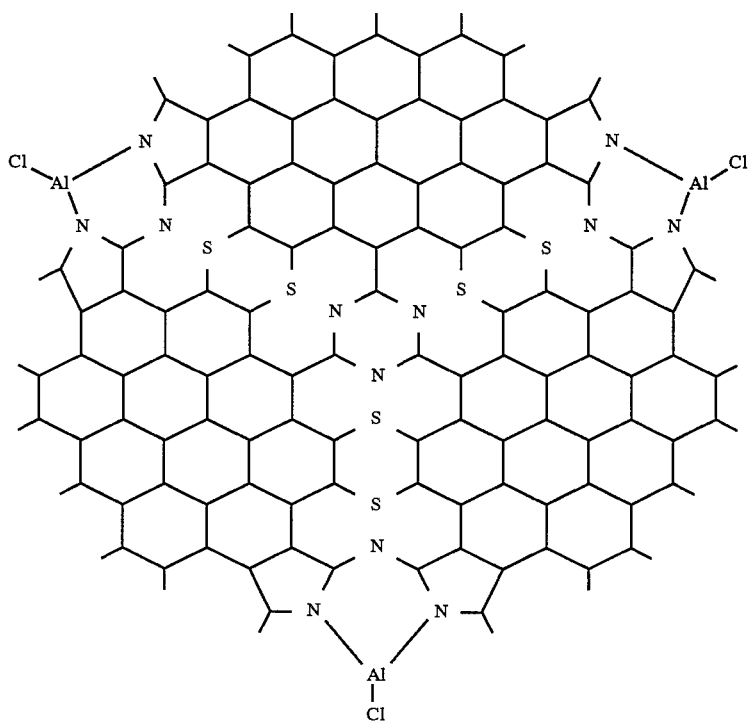

EXAMPLE 3

Instead of filling the spheres with bromocyanide according to example 1, it is possible to fill the spheres with sulphonised halogens. These may, together with aluminium chloride, at the same time be used to close the spheres. Aluminium chloride, disulphur dichloride and sulphur dichloride are mixed 1:1. 1 part of empty spheres and 0.25 parts of hydrogen iodide are mixed with 10 parts of the above mixture and then brought to react at a pressure of 30 bars in an automatic stirrer heated to 50° C. for 2 hours. The hydrogen iodide used should contain a small quantity of iodide$^{131}$. The resulting mixture is then treated as in example 2. The spheres thus obtained, containing sulphur dichloride, disulphur dichloride, aluminium chloride and radioactively marked hydrogen iodide as well as small amounts of hydrogen chloride, are defined in partial formula (10). The spheres are washed with acetone and then, in contrast to example 2, treated for 20 minutes at 50° C. with a hydrogen peroxide solution at 10%. When the experience is repeated using sulphur dichloride instead of disulphur dichloride, there is no substantial change in the product mix.

EXAMPLE 4

The spheres filled with bromocyanide and obtained according to example 1, defined by the structure shown in the partial formula (7), are converted in the presence of copper solids and copper I chloride at 220° C., a large excess of boron trichloride and at a pressure of 300 bar in a heated automatic stirrer for 2 hours. The mixture is then cooled, decompressed, filtered and the solids are washed first with water and thereafter with nitric acid 20% until the filtrate does not contain any more copper. The solids are thereafter washed with acetone and dried. The filled spheres obtained in this manner are defined through the partial formula (11).

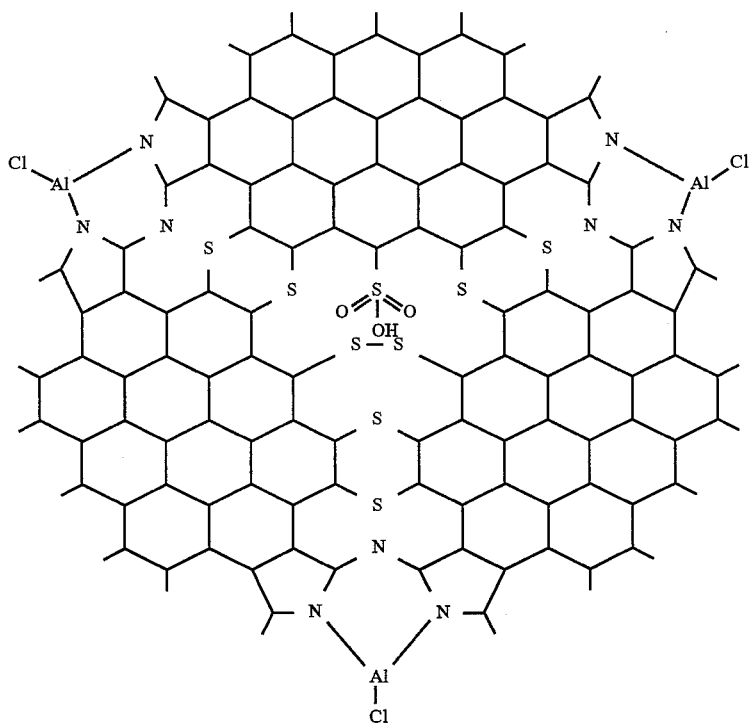

10)

The closure of the spheres, which are described in the partial formula (10), may also be obtained through the use of elemental sulphur at reaction temperatures over 200° C.

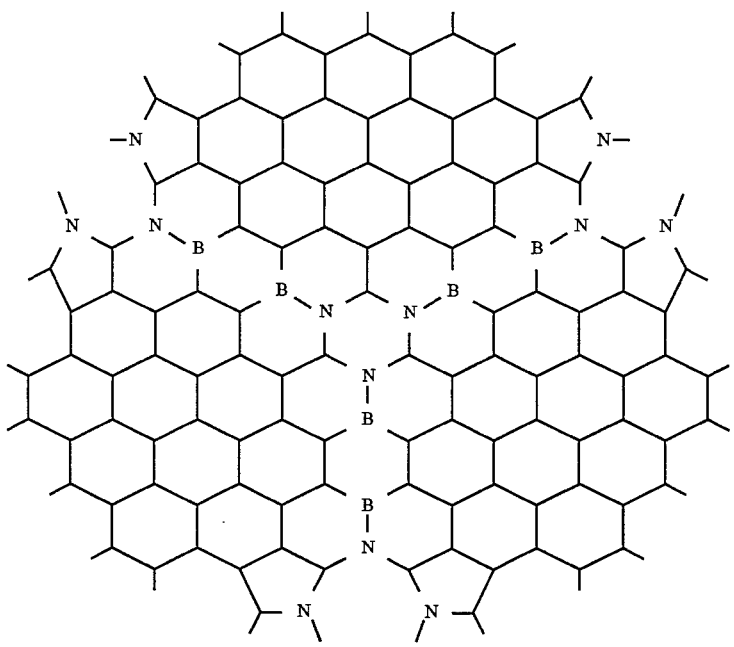

11)

The transformation of the filled spheres, carried out according to example 4 and defined by structure (7), produce heterofullerenes if the spheres present a tetrahedral symmetry and contain four boron halogen coordinated subporphyrin functions. The boron halogen function that is coordinated with the subporphyrin function is de-haloginated through this conversion according to equation (12). Filled heterofullerens are not described in the literature.

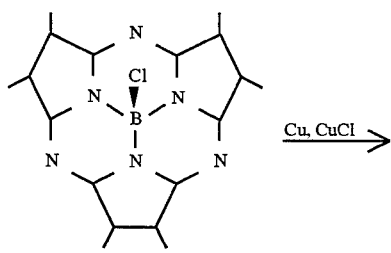

12)

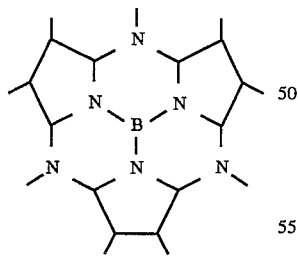

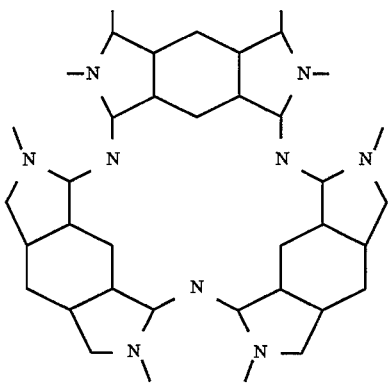

13)

14)

EXAMPLE 5

Spheres, that are defined by the characteristic structural components described in partial formula (13), may be filled and closed under the same reaction conditions as in example 1. The filled, closed spheres are described by structural components defined in partial formula (14).

EXAMPLE 6

The transformation of spheres that are defined by the structural components described in partial formula (13), in a heated automatic stirrer at pressure and temperature conditions of 300 bar and 250° C. respectively, in the presence of a large excess of boron trichloride, copper powder and copper I chloride. Solid ammonium chloride is added after 2 hours and the mixture is left to react for a further 2 hours.

Ammonium chloride is added in a molar relation of 1:1 relative to boron trichloride. The mixture is thereafter cooled and decompressed, extracted with cold water, filtered and the solids are washed with concentrated ammoniac until free of chloride, and then dried. Palladium black, equal to 0.1 of the weight of the added copper powder, is added to the above mixture which contains copper powder and filled spheres consisting of structural components defined in partial formula (15). The mixture is heated to 300° C. under nitrogen, and then cooled after approximately 2 hours, copper and palladium are dissolved in nitric acid and the mixture is filtered, the solids then washed and dried. Spheres filled with boron trichloride and hydrogen chloride are thus obtained; they are defined by structural components according to partial formula (16).

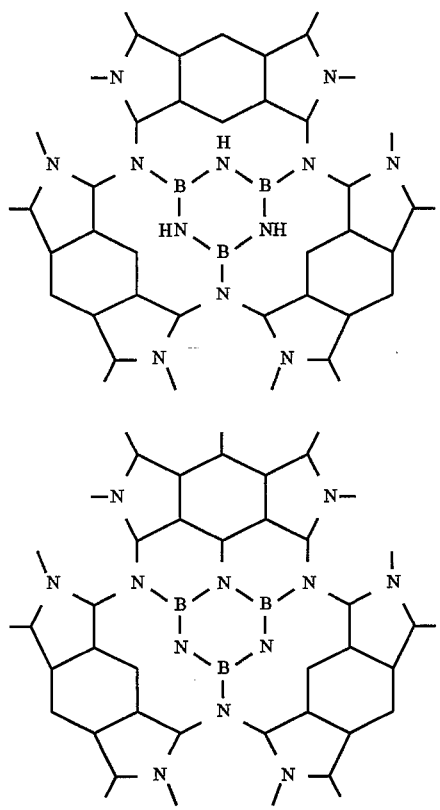

The conversion of filled spheres carried out according to example 6, and using spheres with a tetrahedral symmetry, also produces filled heterofullerenes containing dehalogenated subporphyrin complexes as defined in the schematic formulation (12).

EXAMPLE 7

A mixture of diaminomaleonitrile (100 mmol), amberic acid dinitrile-2,3-dion (70 mmol) and anhydrous acetic acid (1000 mmol) are heated at reflux for 2 hours. The mixture is then put under vacuum, cooled and the precipitated product is filtered, washed with acetic acid and dried on KOH tablets under vacuum. The yellowish crystals obtained are 2,3,5,6,-tetracyanopyrazin (17).

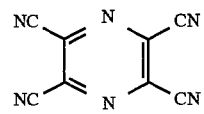

250 g dried uranyl chloride is heated in an automatic stirrer together with 1000 ml pyridin to a temperature of 320° C., and then brought to a pressure of 300 bar through the addition of trimethylamine. 100 g tetracyanopyrazin (17) dissolved in 1000 ml pyridin is slowly added to the above mixture. Two hours after ending the addition, the resulting mixture is left to precipitate, the liquid phase is aspired, decompressed and cooled. The precipitate thus produced is then collected, washed with methanol and dried. A grey-blue powder consisting of spheres characterised by partial formulas (19) to (21) is obtained. The spheres enclose a mixture of pyridine and trimethylamine. The spheres are composed of structural components defined in the partial formulas (19) to (21). The spheres are in addition composed of:

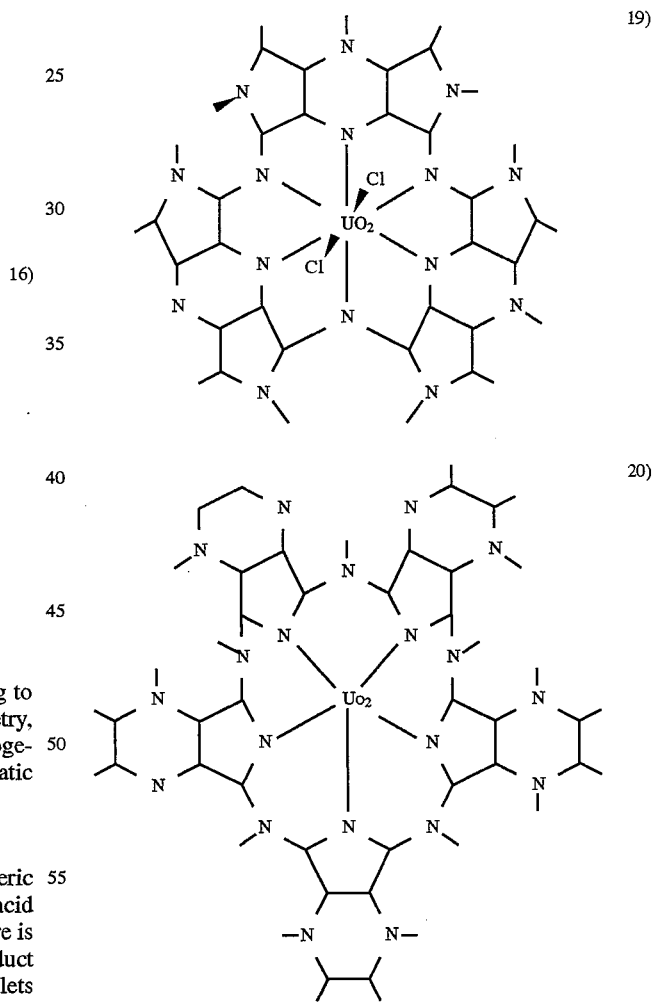

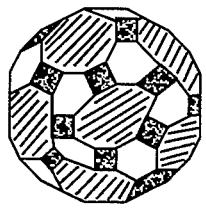

12 Uranyl-superphthalocyanin functions according to partial formulas ($C_{20}$) and the hachured decagons of partial formula (21).

30 pyrazin functions corresponding to the black rectangles in partial formula (21)

20 "N-crownether" functions which are coordinated with uranyl chloride corresponding to partial formula (19) and the white hexagons in partial formula (21)

The spheres are hence described by the complete formula $C_{240}N_{180}O_{64}U_{32}Cl_{40}$ (18). This complete formula does not take the "filling" trimethylamine into consideration. Each sphere presents an icosahedral symmetry and encompasses the same volume as the symmetrically identical fullerene $C_{720}$. This sphere should be considered as a fragmentary derivation of the corresponding CN-heterofullerens containing:

a) 12 apertures with surfaces extending over 15 hexagons and 1 pentagon of the CN-fullerene and b) 20 apertures with surfaces extending over 7 hexagons of the CN-fullerene The apertures are thereby closed, in a) through 12 $N_5UO_2$ functions and in b) through 20 $UO_2Cl_2$ functions.

EXAMPLE 8

300 g copper II chloride is heated to 280° C. in an automatic stirrer with 3 l pyridin and 200 ml dimethylformamide, gaseous ammonia is added until a pressure of 300 bar is reached. A solution of 30 g tetracyanopyrazin (17) in 500 ml pyridin is slowly added. The mixture is left to decant one hour after the above mixture was added, the liquid phase is aspirated, decompressed and cooled. A precipitation occurs, the precipitate is washed with methanol, dried and a dark blue powder is obtained. This is composed of spheres filled with pyridin and ammonia. The spheres are composed of the structural components defined in partial formulas (22) to (24). The spheres are in addition composed of:

6 copper phthalocyanin functions corresponding to the partial formula (22) and to the hachured octogons in partial formula (24)

12 pyrazin functions corresponding to the black rectangles in partial formula (24)

8 "N-crownether" functions coordinated with copper II chloride corresponding to partial formula (23) and the white hexagons in partial formula (24)

The spheres thus correspond to the complete formula $C_{96}N_{72}Cu_{14}Cl_{16}$ (25). This complete formula does not take the pyridin/ammonia "filling" into account. The spheres present an octhedral symmetry. They encompass the same volume as the symmetrically identical fullerene $C_{276}$. They are a fragmentary derivation of the corresponding CN-heterofullerene and contain:

a) 6 apertures with surfaces extending over 10 hexagons and 2 pentagons of the CN-fullerene and b) 8 apertures with surfaces extending over 7 hexagons of the CN-fullerene The apertures are thereby closed through, in a) 6 $N_4Cu$ functions and in b) 8 $CuCl2$ functions.

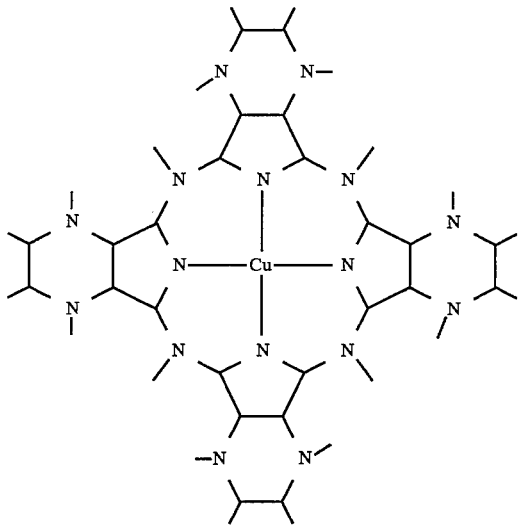

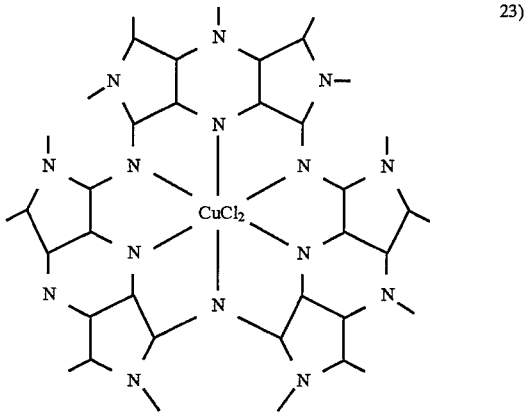

EXAMPLE 9

120 g boron trifluoride and 200 g benzol are heated to 280° C. under nitrogen at 300 bar in an automatic stirrer. A solution of 10 g tetracyanopyrazin (17) in 1.5 l cyclohexane is slowly added to the above mixture. 2 hours after adding the solution, and after cooling the mixture to 150° C., a suspension of 1 part sodium and 6 parts naphthalene is slowly added. This addition is carried out slowly and in small portions.

The temperature is maintained at 150° C. as well as the pressure at 300 bar. The addition of the sodium/naphthalene suspension is stopped when no more component reacting to acids is present. The temperature is thereafter increased to 280° C., kept at this temperature for half an hour, then left to settle and the fluid phase is aspirated, decompressed and cooled. The mixture is filtered, the solids washed with water, then with acetone and dried. The dried remains are brown. They are composed of spheres filled with borontrifluoride, benzol and cyclohexane and which are defined by partial formulas (26) to (28). The spheres are in addition composed of:

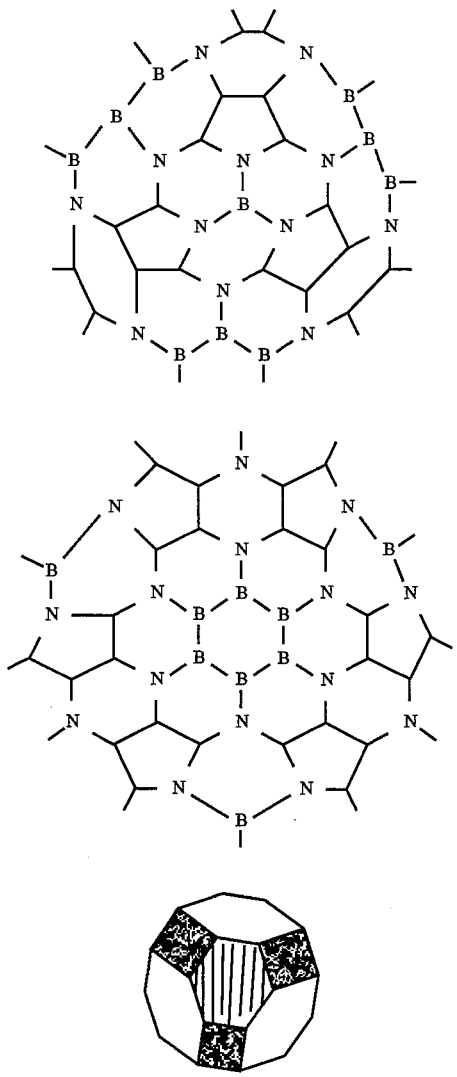

26)

27)

28)

- 4 boron subphthalocyanin functions corresponding to the partial formula (26) and the hachured hexagons in partial formula (28)
- 4 boron hexagonal rings with a "N-crownether" function coordinated according to the partial formula (27) and the white hexagons in partial formula (28)
- 6 pyrazin functions corresponding to the black hexagons in the partial formula (28)

The spheres thus correspond to the complete formula $C_{48}B_{28}N_{36}$ (29). This complete formula does not take the molecules filling the spheres into account. The spheres present a tetrahedral symmetry. They encompass the same volume as the symmetrically identical fullerene $C_{112}$. The spheres are filled CBN-heterofullerenes.

EXAMPLE 10

120 g boron trichloride, 600 g propane and 200 g isobutane are heated to 270° C. under methane at 300 bar in an automatic stirrer. A solution of 10 g tetracyanopyrazin (17) in 300 ml n-pentane is slowly added to the above mixture. The mixture is subsequently left under reaction conditions for 2 hours, a solution of 50 g copper II chloride in 500 ml pyridin is added and the mixture is again left under reaction conditions for 2 hours. The mixture is left to settle, the fluid phase is aspirated, decompressed and cooled. The precipitate formed is washed with water until free of chloride, and thereafter dried. The powdery solids obtained consist of spheres filled with methane, propane, isobutane and n-pentane, defined by partial formulas (30) to (32). The spheres are in addition composed of:

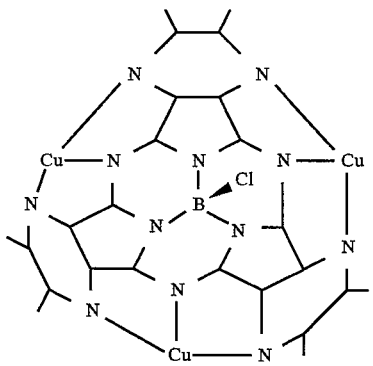

30)

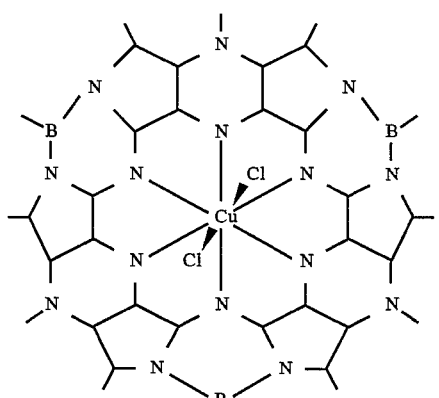

31)

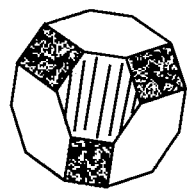

32)

- 4 monochloroboron-sulphthalocyanin functions corresponding to partial formula (30) and the hachured hexagons in partial formula (32)
- 4 copper II chloride coordinated "N-crownether" functions corresponding to partial formula (31) and the white hexagons of partial formula (32)
- 6 pyrazin functions corresponding to the black rectangles of partial formula (32)

The spheres thus correspond to the complete formula $C_{48}N_{36}B_4Cu_4Cl_{12}$ (33). This complete formula does not take the molecules filling the spheres into account. The spheres present a tetrahedral symmetry. They encompass the same volume as the symmetrically identical fullerene $C_{112}$. The spheres are fragmentally derived from the corresponding CBN-heterofullerenes and contain:

- 4 apertures with surfaces extending over 7 hexagons of the CBN-heterofullerene The apertures are closed through 4 $CuCl_2$ functions.

EXAMPLE 11

250 g dried uranyl chloride, 800 g dimethyl formamide and 800 ml trifluoro acetic acid amide are heated to 240° C. under nitrogen at 300 bar in an automatic stirrer. A solution of 30 g hexaazatriphenylenhexacarbonitrile (34) in 300 ml pyridin is slowly added. The mixture is subsequently left under reaction conditions for 2 hours, left to settle, the fluid phase is aspirated, cooled and decompressed. The resulting precipitate is washed first with water and then with methanol and dried. The grey-blue powder thus obtained consists of spheres filled with dimethylformamide, trifluoro acetic acid amide and pyridine, which are defined by partial formulas (35) to (37). The spheres are in addition composed of:

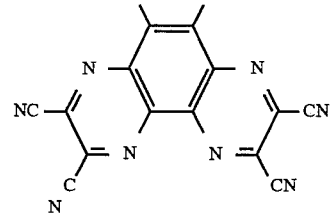

34)

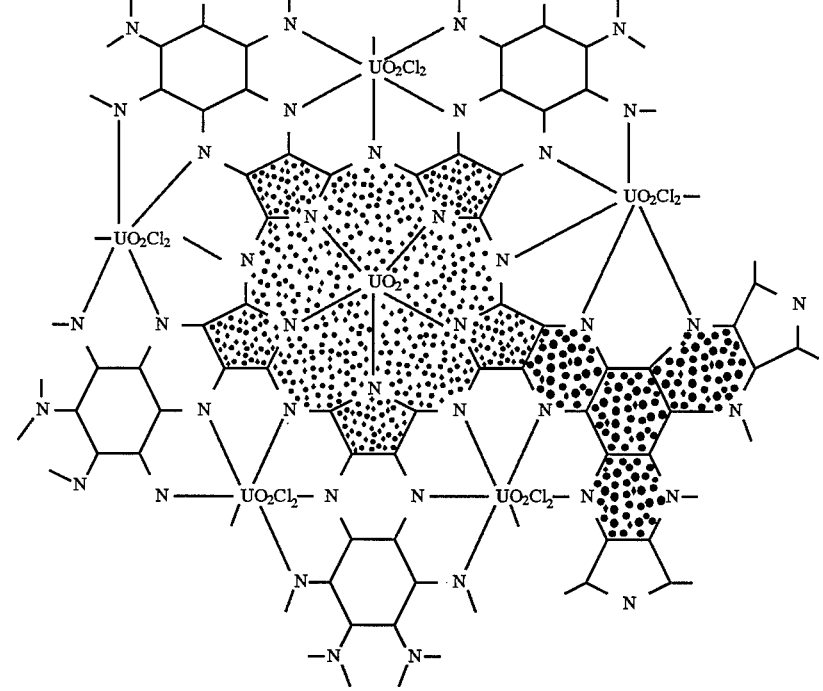

35)

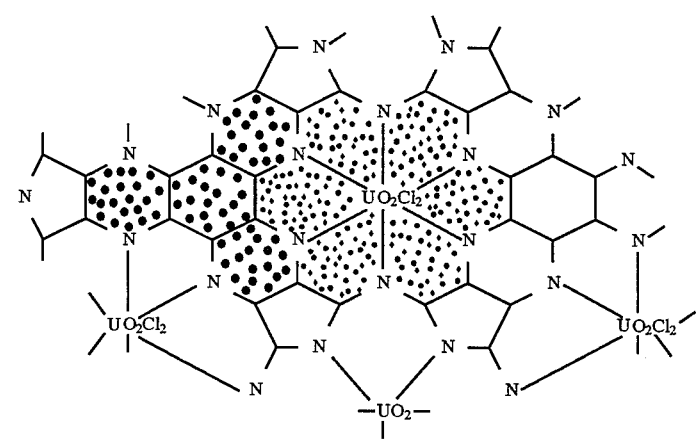

36)

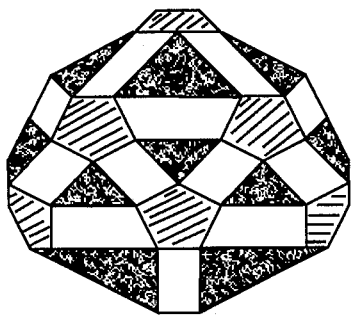

2 uranylsuperporphyrin functions corresponding to partial formula (35), the finely dotted areas and the hachured pentagons in partial formula (37)

30 uranylchloride coordinated "N-crownether" functions corresponding to partial formula (36), the finely dotted areas and the white rectangles of partial formula (37)

20 hexaazatriphenylene functions corresponding to partial formulas (35) and (36), the coarsly dotted areas end the black triangles of partial formula (37).

The spheres thus correspond to the complete formula $C_{360}N_{240}O_{84}U_{42}Cl_{60}(38)$. The complete formula does not take the molecules filling the spheres into account. The spheres present an icosohedral symmetry and encompass the same volume as the symmetrically identical fullerene $C_{960}$. The spheres are fragmentally derived from the corresponding CN-heterofullerenes and contain:

a) 12 apertures with surfaces extending over 15 hexagons and 1 pentagon of the CN-heterofullerene and b) 30 apertures with surfaces extending over 7 hexagons of the CN-heterofullerene The apertures are thereby closed through, in a) 12 $N_5UO_2$ functions and in b) 30 $UO_2Cl_2$ functions.

EXAMPLE 12

In some cases it could be of advantage to use spheres with a hydrophilic surface, e.g. the reaction of tumor antibodies with spheres in aqueous solutions. The surfaces of hydrophobic spheres can be rendered hydrophilic by attaching hydrophilic functions to their surfaces. This can advantageously be done through, for example, a sulphonation with chlorosulphuric acid in excess, at temperatures between the ambient temperature and 120° C. The sulphonic acid groups attached to the surface may also be used to close the spheres.

Spheres with structures corresponding to partial formula (6) are heated to between 80° C. and 90° C. in the presence of a large excess of chlorosulfonic acid and under an HCl and $SO_2$ (1:1) pressure of 300 bar in an automatic stirrer, and then left under these conditions for 30 minutes.

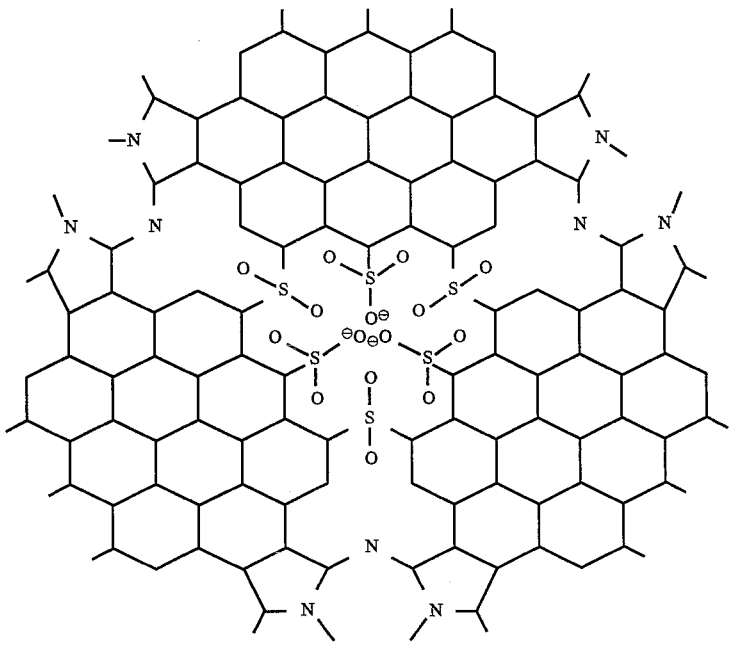

The mixture is thereafter decompressed and the spheres are washed through several ultracentrifugations, decantations and slurrying with water, neutralised with soda lye and isolated as a solution at approximately 5%. The spheres containing $SO_2$ and HCl, present a sulphonic or sulphonate content approximating to the spheres defined in partial formula (39). The sulphonated groups may be used to join these spheres with others containing adequate functional groups.

The production of hermetically closed spheres of a novel structure and containing selected molecules is shown in the above examples for the first time. The opening of the spheres can successfully be carried out through the invented procedure by using radiation at wavelengths between 600 nm and 750 nm, and also at wavelengths shorter than 400 nm. It is preferable to use the longer wavelengths for certain applications of the spheres, e.g. medicin. It is preferable to use infrared radiations for some specific uses of the spheres, e.g. ignition at a distance of spheres filled with exothermically reacting materials like explosives. An uncomplicated procedure to open the spheres is shown in example 13.

EXAMPLE 13

Spheres having an icosahedrical symmetry and described by the complete formula $C_{1080}H_{300}N_{120}O_{24}U_{12}$, that have the same volume as the symmetrically identical fullerene $C_{1620}$, that are produced according to DOS 41 14 536 A1, Example 9, and that are defined by the partial formula (6) are filled and sulphonated according to Example 10. The neutral 5% aqueous solution of spheres is diluted to 0.5 g spheres per liter. Indicator paper is then sprayed on one side with this solution. Ruby red light of a wavelength of 695 nm and with an intensity that does not destroy the cellulosa thermically, is guided onto the paper through the use of optical fibres. It is possible to observe the tracing of the laser beam on the back of the indicator paper: the opened spheres release acid which colours the paper red. The hydrogen chloride and sulphur dioxide released from the spheres react with the humidity in the paper where the laser beam has opened the spheres.

EXAMPLE 14

Filled spheres partially constructed from porphyrins were produced in order to prove that filling the spheres according to the invented method also succeeds in the case of nitrogen-poor porphyrins. Spheres with an octahedral symmetry and described by the complete formula $C_{192}H_{108}N_{24}$ were produced according to DOS P 41 14 536. A1. These spheres contain functions defined in partial formulas (40) and (41) and they encompass the same volume as the symmetrically identical fullerene $C_{372}$.

10 g of spheres, 200 g aluminium tribromide and 50 g sulphur are heated to 120° C. in an automatic stirrer and left to react for 4 hours. The mixture is then cooled and extracted with perchlorethylene and elemental sulphur. The perchlorethylene is then distilled off, 200 g aluminium tribromide is again added and the mixture is heated to 120° C. 60 g silver bromide is then added and left to react for 2 hours. The resulting mixture is cooled, extracted with perchlorethylene from the excess of aluminium tribromide and then extracted from the excess of silver bromide with ammonia. The reaction has to be carried out in the dark due to the light sensitivity of silver bromide. The extraction residue is then washed with water and dried. The grey-black powder obtained contains a majority of spheres filled with aluminium tribromide, which are defined by the structural components shown in formula (42) and (43). The spheres have thus the complete formula $C_{192}S_{48}Al_6Ag_8Br_{14}$ (44). The content of the spheres is not taken account of in the complete formula (44).

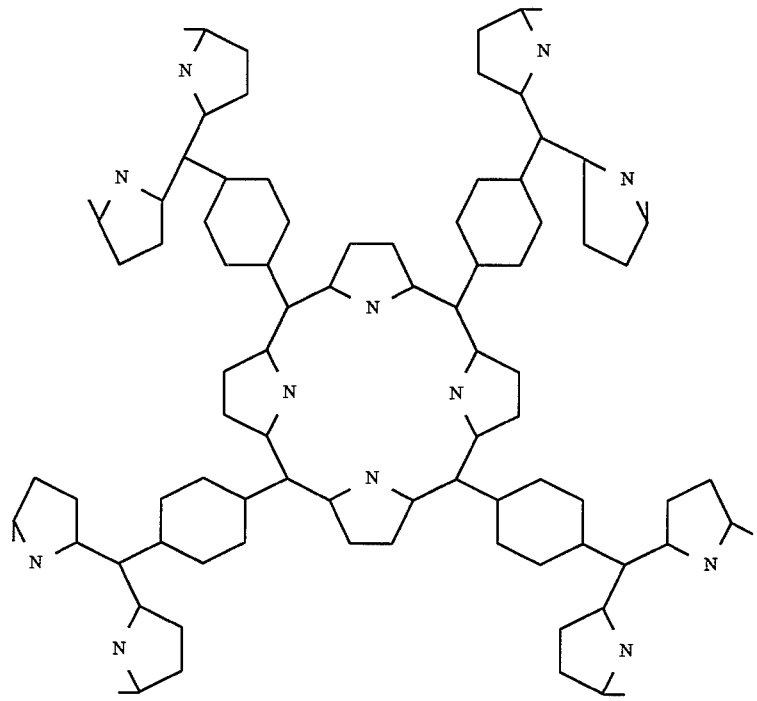

40)

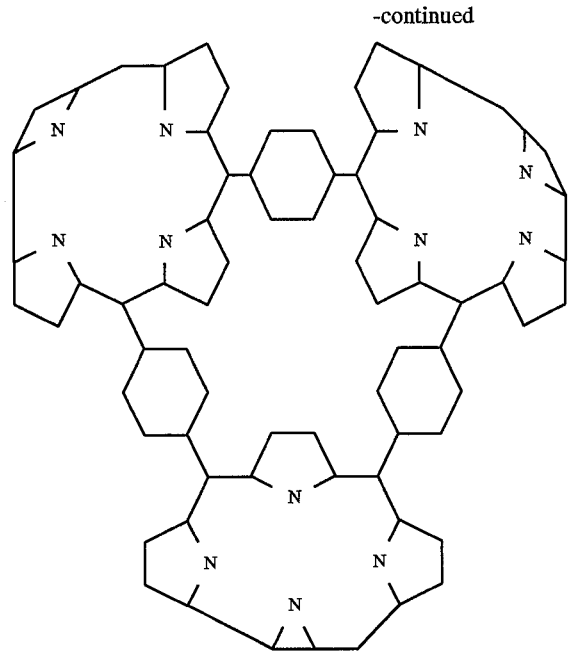
41)
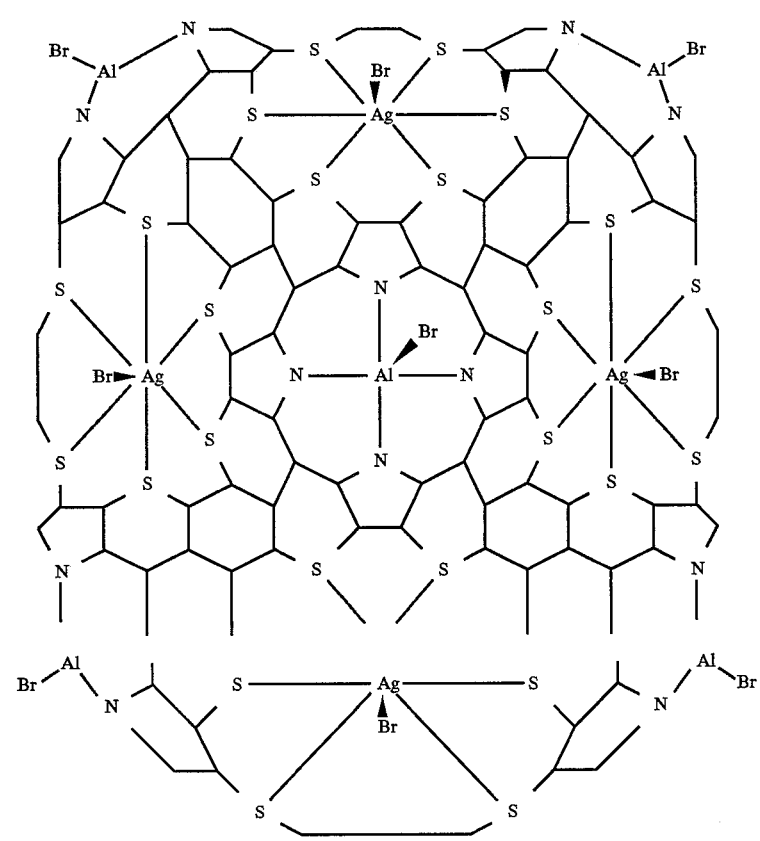
42)

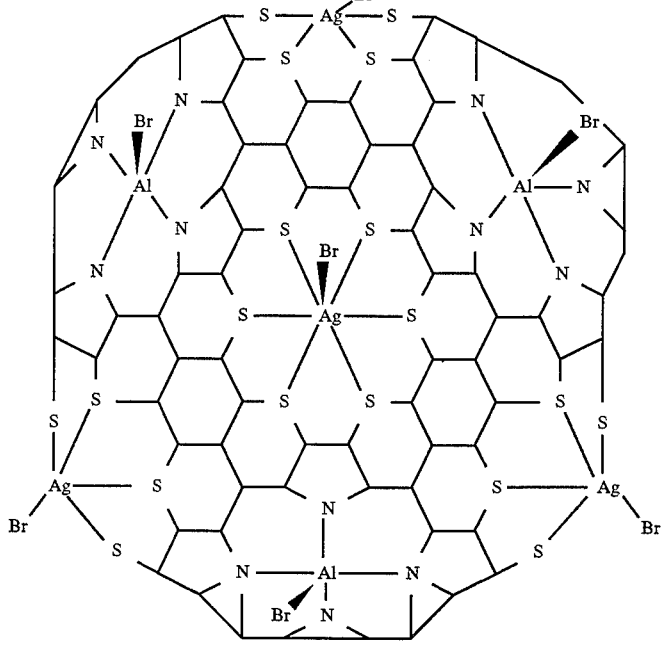

43)

I claim:

1. The method of releasing active compounds from spheres of tetrahedral, octahedral or icosahedral symmetry, filled with active compounds, the spheres encompassing nearly the same volume as symmetrically identical fullerenes, comprising the step of irradiating the spheres so that the spheres are destroyed to release the active compounds.

2. The method of releasing active compounds from the spheres filled with active compounds according to claim 1, wherein the spheres are irradiated with laser light.

3. A method according to claim 1, wherein the spheres are irradiated with photons of a wavelength between 400 nm and 750 nm.

4. A method according to claim 1, wherein the spheres are irradiated with infrared light.

5. A method according to claim 1, wherein the spheres are from about 1 nm to about 10 nm in diameter.

* * * * *

UNITED STATES PATENT AND TRADEMARK OFFICE
CERTIFICATE OF CORRECTION

PATENT NO. : 5,627,353
DATED : May 6, 1997
INVENTOR(S) : Franz D. Oeste

It is certified that error appears in the above-indentified patent and that said Letters Patent is hereby corrected as shown below:

On the title page item [73] delete:
 -- 73 Assignee: Udo Schlagwein, Bad Nauheim, Germany --.

Signed and Sealed this

Thirteenth Day of April, 1999

Attest:

Q. TODD DICKINSON

*Attesting Officer*     *Acting Commissioner of Patents and Trademarks*